United States Patent
Mathews et al.

(10) Patent No.: US 12,306,173 B2
(45) Date of Patent: May 20, 2025

(54) CAMERA-BASED HEMOGLOBIN DETECTION

(71) Applicant: THE JOHNS HOPKINS UNIVERSITY, Baltimore, MD (US)

(72) Inventors: Simon C. Mathews, Baltimore, MD (US); Amit Banerjee, Silver Spring, MD (US); Pankaj Jay Pasricha, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/699,417

(22) PCT Filed: Sep. 7, 2022

(86) PCT No.: PCT/US2022/042692
§ 371 (c)(1),
(2) Date: Apr. 8, 2024

(87) PCT Pub. No.: WO2023/064053
PCT Pub. Date: Apr. 20, 2023

(65) Prior Publication Data
US 2024/0410875 A1    Dec. 12, 2024

Related U.S. Application Data

(60) Provisional application No. 63/256,203, filed on Oct. 15, 2021.

(51) Int. Cl.
*G01N 33/483* (2006.01)
*G01N 21/17* (2006.01)
(Continued)

(52) U.S. Cl.
CPC ....... *G01N 33/4833* (2013.01); *G01N 21/314* (2013.01); *G01N 33/53* (2013.01);
(Continued)

(58) Field of Classification Search
CPC .. G01N 33/4833; G01N 21/314; G01N 33/53; G01N 33/68; G01N 2021/1765;
(Continued)

(56) References Cited

U.S. PATENT DOCUMENTS

2013/0023744 A1    1/2013  Benni
2017/0089761 A1    3/2017  McQuilkin et al.
(Continued)

FOREIGN PATENT DOCUMENTS

WO    2020172073 A1    8/2020

OTHER PUBLICATIONS

"Zbynek Malenovsky et. al., Retrieval of Spruce Leaf Chlorophyll Content from Airborne Image Data Using Continuum Removal and Radiative Transfer, 2013, Remote Sensing of Environment, 85-102" (Year: 2013).*

(Continued)

*Primary Examiner* — Andrae S Allison
*Assistant Examiner* — Phuong Hau Cai
(74) *Attorney, Agent, or Firm* — MH2 Technology Law Group LLP

(57) ABSTRACT

A method for detecting a molecule in a sample includes applying a first filter to an image at a first wavelength. The method also includes applying a second filter to the image at a second wavelength. The method also includes applying a third filter to the image at a third wavelength. The first, second, and third wavelengths are within a predetermined wavelength range, and wherein first, second, and third wavelengths are different from one another. The method also includes detecting a spectral signature for the molecule in the sample in the image after the first, second, and third filters are applied to the image. The method also includes determining whether the molecule is present in the sample based at least partially upon the detected spectral signature.

14 Claims, 5 Drawing Sheets

(51) Int. Cl.
*G01N 21/31* (2006.01)
*G01N 33/53* (2006.01)
*G01N 33/68* (2006.01)

(52) U.S. Cl.
CPC ..... *G01N 33/68* (2013.01); *G01N 2021/1765* (2013.01); *G01N 2021/3174* (2013.01); *G01N 2333/805* (2013.01)

(58) Field of Classification Search
CPC ..... G01N 2021/3174; G01N 2333/805; G01N 2021/3148; G01N 21/31; G01N 33/721; A61B 5/14535; A61B 5/0075; G01J 3/32; G01J 2003/2806; G01J 3/2803; G01J 3/42; G01J 3/28
See application file for complete search history.

(56) References Cited

U.S. PATENT DOCUMENTS

| | | | |
|---|---|---|---|
| 2019/0195802 A1 | 6/2019 | Attar et al. | |
| 2021/0075978 A1 | 3/2021 | Sowa et al. | |
| 2021/0139948 A1 | 5/2021 | Bitenc et al. | |
| 2021/0181020 A1* | 6/2021 | McQuilkin | G01N 21/31 |

OTHER PUBLICATIONS

"Naoto Yokoya et. al., Potential of Resolution-Enhances Hyperspectral Data for Mineral Mapping Using Simulated EnMAP and Sentinel-2 Images, Dec. 2015, Special Issue the Environment Mapping and Analysis Program Mission: Preparing for Its Scientific Exploitation, Remote Sens. 2016, 8[3], 172" (Year: 2015).*
"Gregg A. Swayze et. al., Characterizing the Source of Potentially Asbestos-Bearing Commercial Vermiculite Insulation using in situ IR Spectroscopy, Mar. 2018, De Gruyter" (Year: 2018).*
Lee, S. (Authorized officer), International Preliminary Report on Patentability in corresponding International Application No. PCT/US2022/042692 mailed on Apr. 25, 2024, 16 pages.
Rodriquez, K. (Authorized officer), International Search Report and Written Opinion in corresponding International Application No. PCT/US2022/042692 mailed on Jan. 27, 2023, 21 pages.

* cited by examiner

CAMERA-BASED HEMOGLOBIN DETECTION

CROSS-REFERENCE TO RELATED APPLICATIONS

This application is the national stage entry of International Patent Application No. PCT/US2022/042692, filed on Sep. 7, 2022, and published as WO 2023/064053 A1 on Apr. 20, 2023, which claims priority to U.S. Provisional Patent Application No. 63/256,203, filed on Oct. 15, 2021, which are hereby incorporated by reference herein in their entireties.

FIELD OF THE DISCLOSURE

The present disclosure relates generally to systems and methods for detecting a molecule in a sample. More particularly, the present disclosure relates to systems and methods for camera-based (e.g., spectral-based) hemoglobin detection in a stool sample.

BACKGROUND OF THE DISCLOSURE

A colonoscopy is an endoscopic procedure that is commonly used to screen for colorectal cancer or to detect other abnormalities in the large intestine and rectum. During a colonoscopy, a long, flexible tube (i.e., a colonoscope) is inserted into the rectum. A tiny video camera at the tip of the tube allows the doctor to view the inside of the entire colon. If necessary, polyps or other types of abnormal tissue can be removed through the scope during a colonoscopy. Tissue samples (e.g., biopsies) can be taken during a colonoscopy as well. However, it would be useful to have systems and methods that provide an alternative to screening for colorectal cancer that is both convenient and non-invasive.

SUMMARY

In accordance with an aspect of the present disclosure, a method for detecting a molecule in a sample is disclosed. The method includes applying a first filter to an image at a first wavelength. The method also includes applying a second filter to the image at a second wavelength. The method also includes applying a third filter to the image at a third wavelength. The first, second, and third wavelengths are within a predetermined wavelength range, and wherein first, second, and third wavelengths are different from one another. The method also includes detecting a spectral signature for the molecule in the sample in the image after the first, second, and third filters are applied to the image. The method also includes determining whether the molecule is present in the sample based at least partially upon the detected spectral signature.

A method for detecting hemoglobin in a stool sample is also disclosed. The method includes capturing an image of the stool sample with a camera. The method also includes applying a first bandpass filter to the image at a first wavelength as the image is captured. The method also includes applying a second bandpass filter to the image at a second wavelength as the image is captured. The method also includes applying a third bandpass filter to the image at a third wavelength as the image is captured. The first, second, and third wavelengths are between 450 nm and 690 nm. The third wavelength is between the first and second wavelengths. The method also includes detecting a spectral signature for the hemoglobin in the stool sample in the image after the first, second, and third bandpass filters are applied to the image. The spectral signature includes an absorption feature. Detecting the spectral signature includes performing continuum removal on the spectral signature between 450 nm and 690 nm using linear interpolation to remove a slope from the spectral signature while maintaining the absorption feature. Performing the continuum removal includes determining a first product of a weight and a value of the absorption feature at the first wavelength, determining a second product of a complement of the weight and a value of the absorption feature at the second wavelength, and determining a sum of the first product and the second product. Detecting the spectral signature also includes determining a band ratio of the absorption feature for each pixel in the image. The band ratio includes a ratio of the sum and the value of the absorption feature at the third wavelength. The method also includes aggregating the band ratios for the pixels in the image. The method also includes determining that the hemoglobin is present in the stool sample based at least partially upon the aggregation of the band ratios.

A system for detecting a molecule in a sample is also disclosed. The system includes a camera configured to capture an image of the sample. The system also includes a computing system. The computing system is configured to detect a spectral signature for the molecule in the sample in the image after first, second, and third filters are applied to the image. The computing system is also configured to determine whether the molecule is present in the sample based at least partially upon the detected spectral signature.

DETAILED DESCRIPTION OF THE PREFERRED EMBODIMENTS

The presently disclosed subject matter now will be described more fully hereinafter with reference to the accompanying Drawings, in which some, but not all embodiments of the disclosures are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Figure 1:
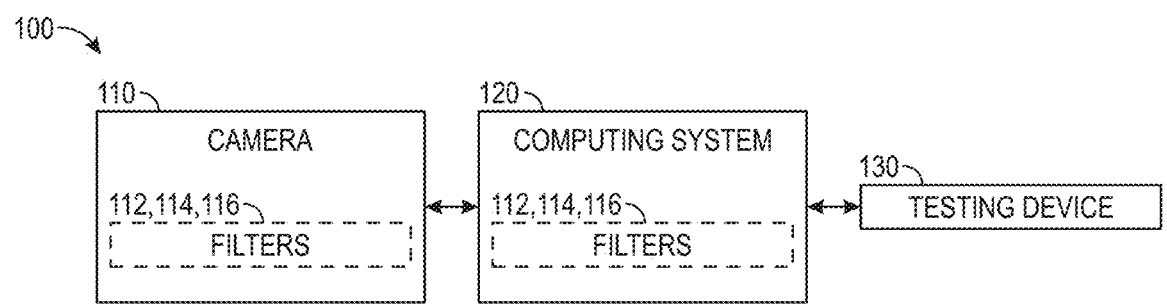
FIG. 1 illustrates a schematic view of a system for identifying a molecule in a sample, according to an embodiment.
Figures 2A, 2B:
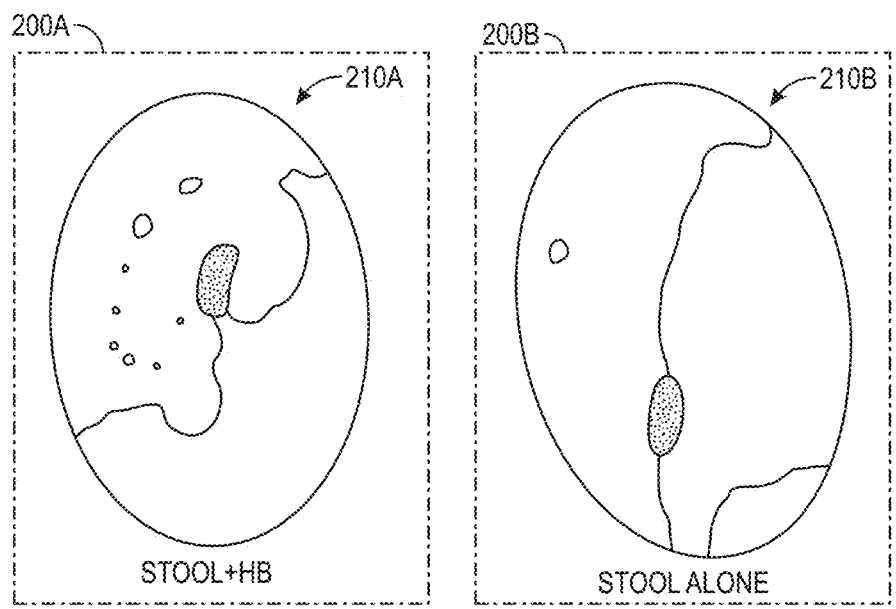
FIG. 2A illustrates an image of a sample of stool with hemoglobin therein.
FIG. 2B illustrates an image of a sample of stool alone (i.e., with no hemoglobin), according to an embodiment.

FIG. 1 illustrates a schematic view of a system 100 for identifying a molecule in a sample, according to an embodiment. The molecule may be or include hemoglobin, bilirubin, calprotectin, albumin, fatty acid, hydrogen sulfide, and others. The sample may be or include stool, urine, saliva, another biologic specimen, or a combination thereof. FIG. 2A illustrates an image 200A of a sample 210A of stool with hemoglobin therein, and FIG. 2B illustrates an image 200B of a sample 210B of stool alone (i.e., with no hemoglobin), according to an embodiment.

The system 100 may include a camera 110, a computing system 120, and a testing device 130. In one embodiment, the camera 110, the computing system 120, the testing device 130, or a combination thereof may be co-located in a single device. For example, at least a portion of the system 100 may include, be a part of, or connect to a smartphone, a tablet, a laptop, or the like. The camera 110 may be configured to capture one or more images (e.g., images 200A, 200B) of the sample (e.g., sample 210A, 210B), which may or may not have the molecule therein. One or more filters (e.g., three are shown: 112, 114, 116) may be applied as part of the capture of the images 200A, 200B. In one embodiment, the filters 112, 114, 116, may be applied to the lens of the camera 110. For example, the filters 112, 114, 116 may be or include thin film filters that cover the lens of the camera 110. The film filters may be changed manually so that three images may be captured of a single sample-one image with each filter. In another embodiment, the filters 112, 114, 116 may be built (e.g., directly) into the CCD focal plane of the camera 110. In yet another embodiment, a Bayer pattern filter array may be used. In yet another embodiment, the filters 112, 114, 116 may be applied to the images 200A, 200B by the computing system 120.

Figure 3:
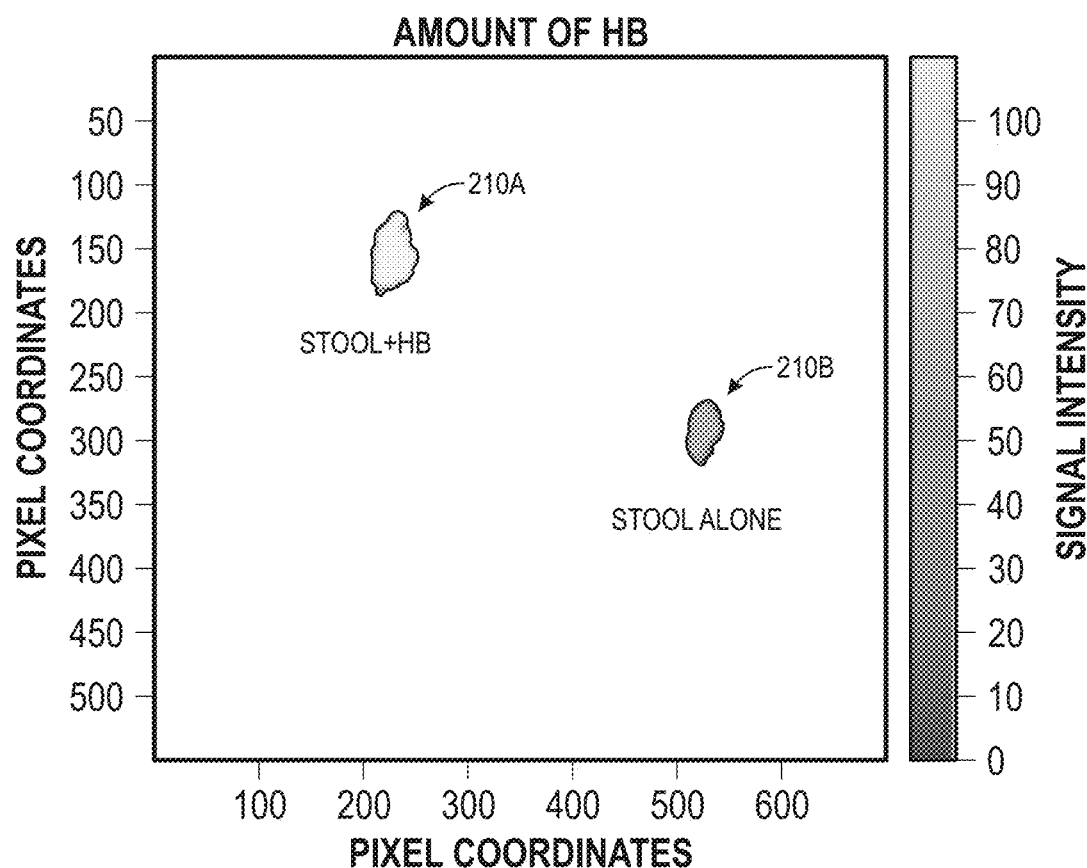
FIG. 3 illustrates a graph showing the sample of stool with hemoglobin versus the sample of stool alone, according to an embodiment.
Figure 4:
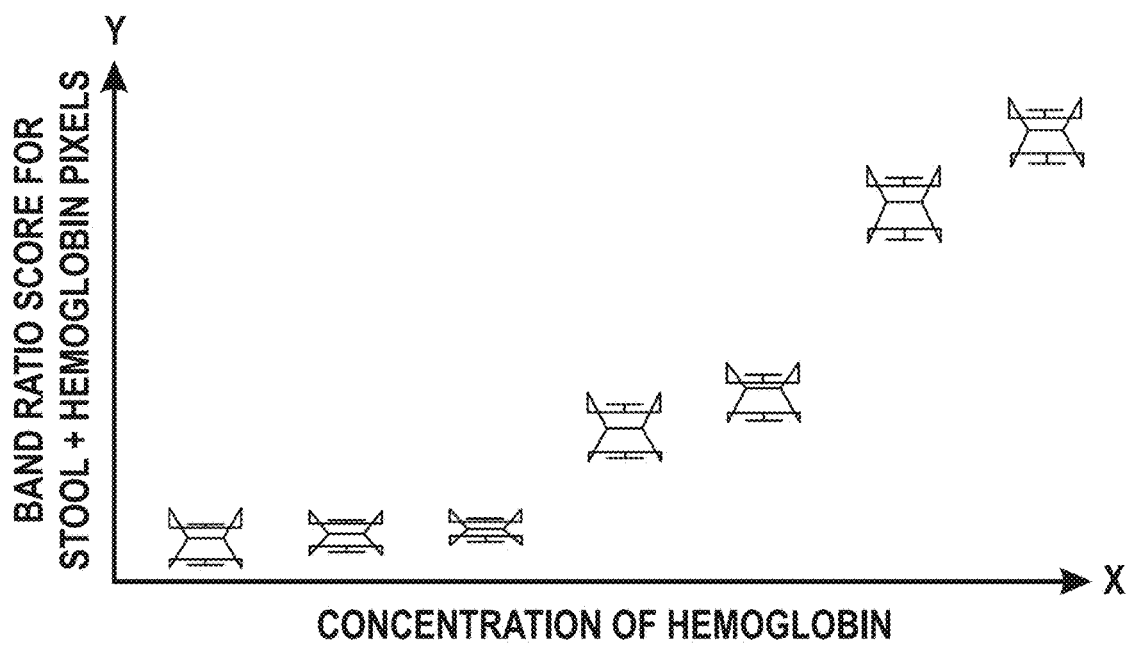
FIG. 4 illustrates a graph showing the dose response in hemoglobin detection as the concentration of the hemoglobin in stool increases, according to an embodiment.

The computing system 120 may be configured to analyze the images 200A, 200B to detect the presence and/or amount of the molecule (e.g., hemoglobin) in the sample (e.g., stool). More particularly, the computing system 120 may be configured to detect a unique spectral signature of the molecule to differentiate between a sample with the molecule versus a sample without the molecule. FIG. 3 illustrates a graph showing the sample 210A of stool with hemoglobin versus the sample 210B of stool alone, according to an embodiment. In one example, as the amount of the molecule in the sample increases, the detectability of the molecule also increases in a dose response manner. This is shown in FIG. 4, which illustrates a graph showing the dose response in hemoglobin detection as the concentration of the hemoglobin in stool increases, according to an embodiment. More particularly, the ratio of specific wavelength features and a quantitative comparison of these resulting values across multiple types of computations may help to distinguish samples with hemoglobin from those without.

The testing device 130 may be or include a fecal immunochemical test (FIT) device or other diagnostic test/information. The testing device 130 may test for the molecule (e.g., hemoglobin) in the sample (e.g., stool) before, simultaneously with, or after the camera 110 and the computing system 120 attempt to detect the presence and/or amount of the molecule in the sample. For example, the testing device 130 may be configured to connect to the computing system 120 and to serve as a secondary testing system for the molecule after the camera 110 and the computing system 120 perform image-based detection.

Figure 5:
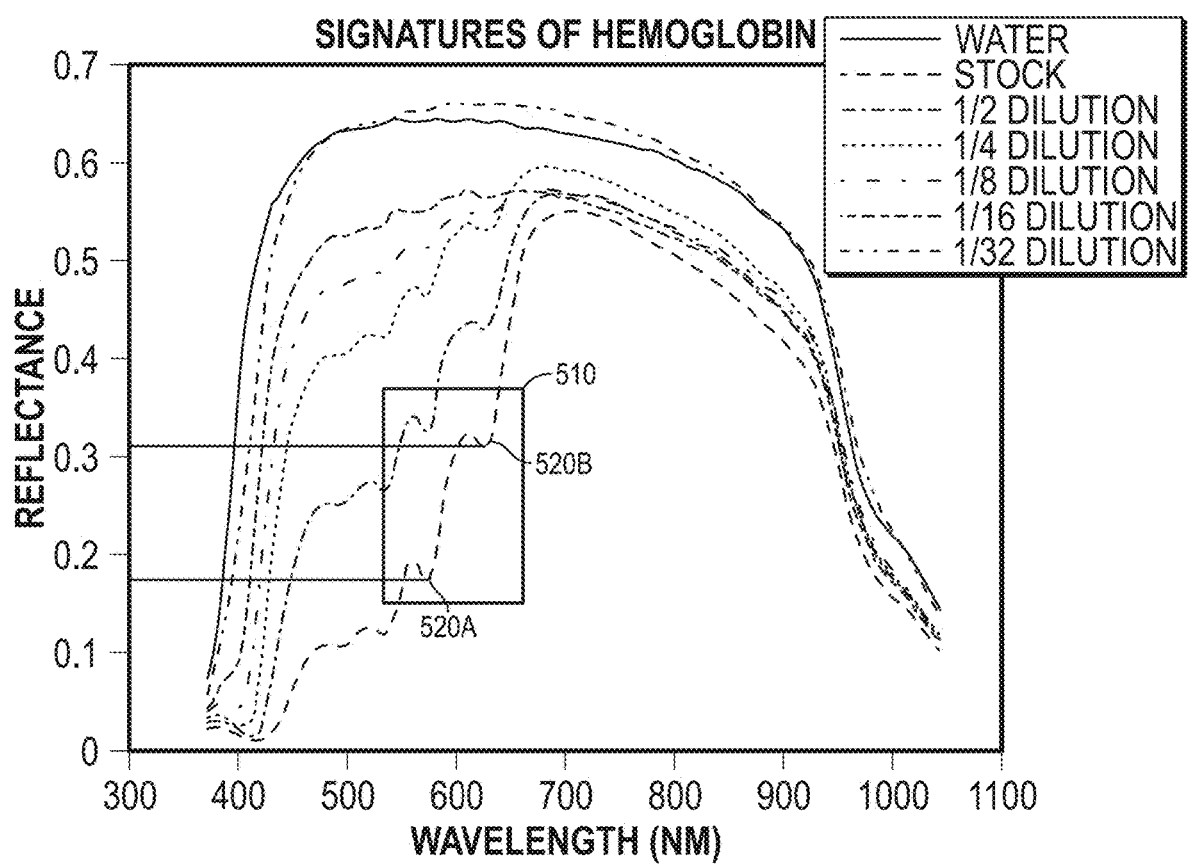
FIG. 5 illustrates a graph showing reflectance versus wavelength of hemoglobin at a plurality of different concentrations, according to an embodiment.

FIG. 5 illustrates a graph showing reflectance versus wavelength of hemoglobin at a plurality of different concentrations, according to an embodiment. Each hemoglobin curve may have one or more spectral signatures (e.g., also referred to as fingerprints) 510 that may be used to detect its presence in various types of samples. The spectral signature 510 may resemble the letter V (also referred to as a V-feature) and/or the letter W (also referred to as a W-feature). The spectral signature 510 may be present within a predetermined wavelength range. The predetermined wavelength range may be from about 450 nm to about 690 nm, about 575 nm to about 625 nm, or about 600 nm to about 650 nm.

As described in greater detail below, the computing system 120 may implement a spectral processing algorithm on the images 200A, 200B to detect the presence of the spectral signature 510 for the molecule (e.g., hemoglobin). To accomplish this, the algorithm may utilize spectral continuum removal and/or band-ratio analysis. The continuum removal may use linear interpolation to remove the slope of the spectral signature 510 while maintaining one or more spectral absorption features 520A, 520B. As used herein, a spectral absorption feature refers to a change in shape of the spectral curve. The continuum removal may be performed within the predetermined wavelength range.

After the continuum removal is performed, the band ratio may then be determined for one or more of the absorption features 520A, 520B to measure the ratio of the absorption feature 520A, 520B, which indicates the amount of the chemical associated with the absorption feature 520A, 520B that is present in the sample. In one embodiment, the reflectance value for the point 520B may represent the numerator, and the reflectance value for the point 520A may be the denominator. The ratio (e.g., numerator/denominator) may be greater than or equal to 1 to be positive (i.e., hemoglobin present).

Figure 6:
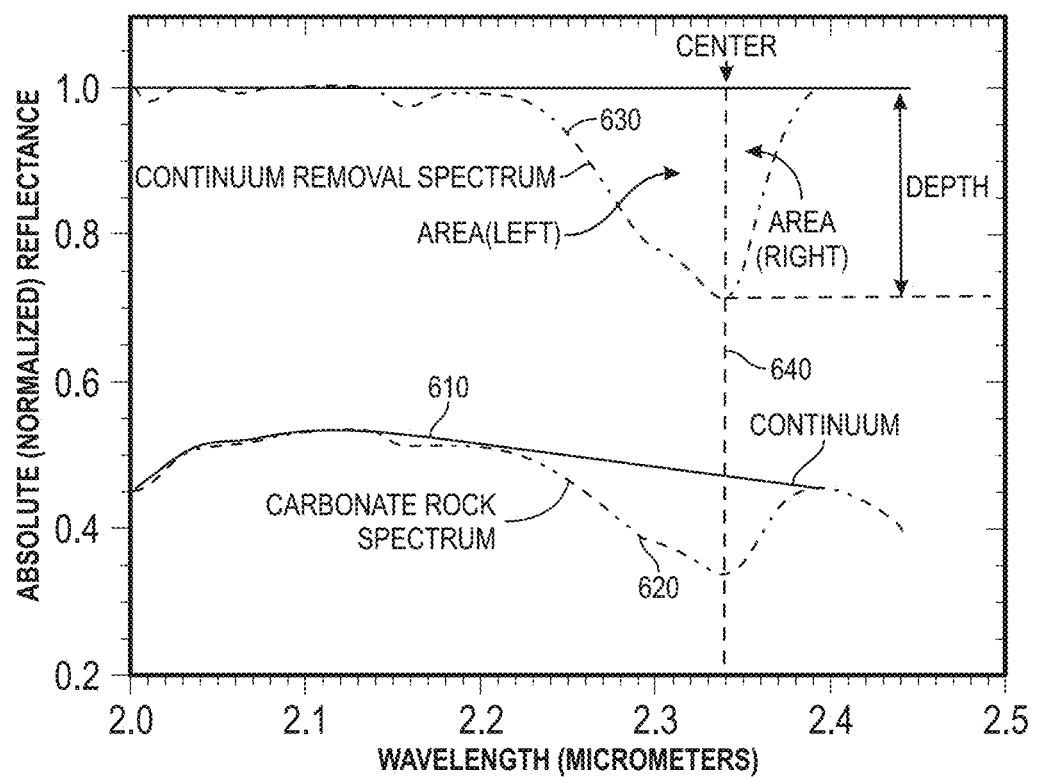
FIG. 6 illustrates a graph showing the detection of a spectral signature in the image, according to an embodiment.

FIG. 6 illustrates a graph showing the detection of a spectral signature in the image, according to an embodiment. The line 610 represents the measured spectrum (e.g., from spectral signature 510). Using interpolation, the spectrum 620 may be determined, which is a measure of the continuum (e.g., the overall shape) of the measured spectrum 610.

The curve 630 may be determined by dividing the spectrum 620 by the spectrum 610. This is referred to as the continuum removal, which effectively removes the overall shape of the measured spectrum 610 and preserves (e.g., enhances) the spectral features (e.g., spectral absorption features 520A, 520B). From the continuum-removed spectrum 630, the spectral depth may be determined using band ratios, as shown along the dashed vertical line 640.

Figure 7:
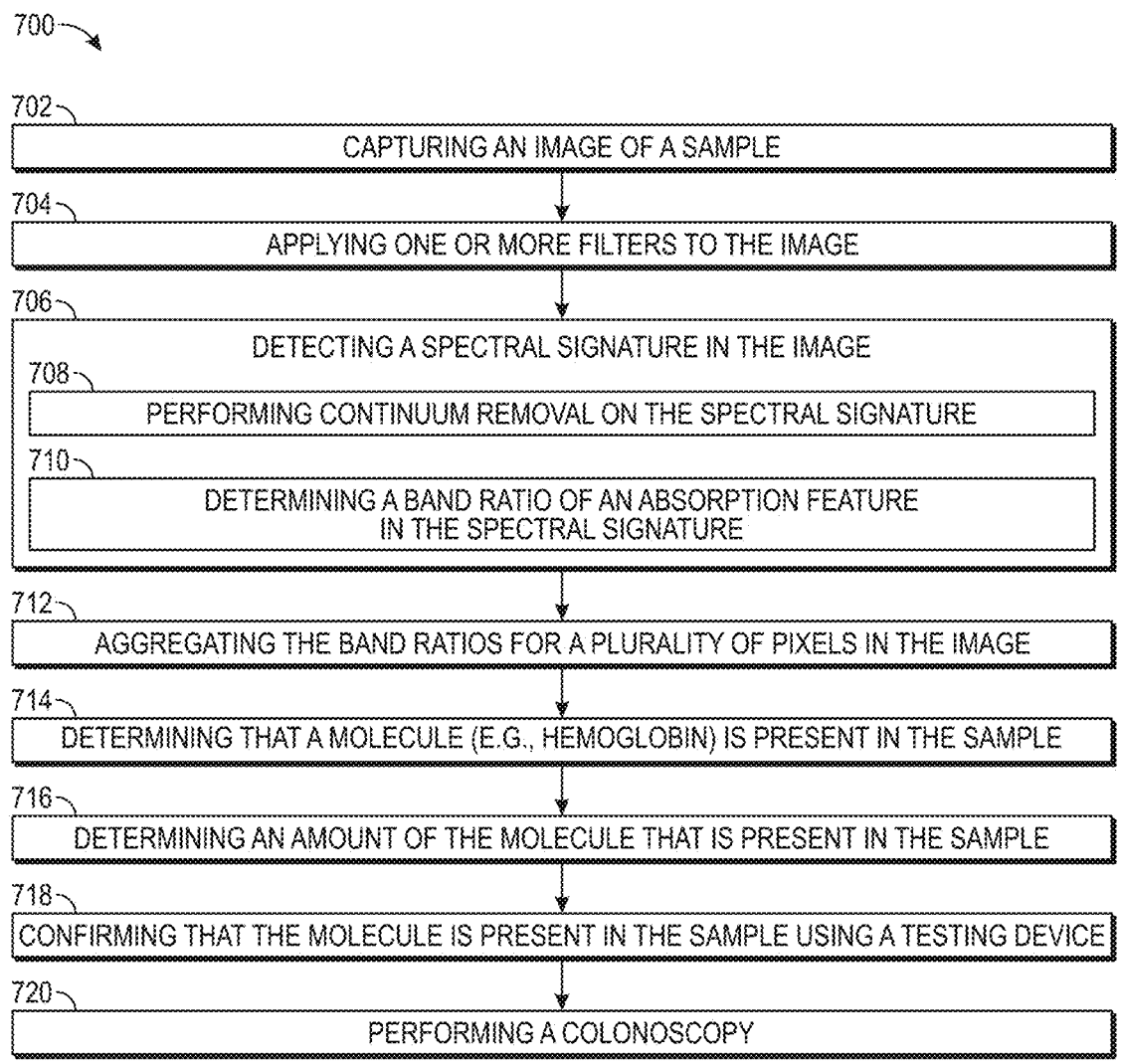
FIG. 7 illustrates a flowchart of a method for detecting a molecule in a sample, according to an embodiment.

FIG. 7 illustrates a flowchart of a method 700 for detecting a molecule in a sample, according to an embodiment. An illustrative order of the method 700 is provided below; however, one or more steps of the method 700 may be performed in a different order, combined, split into substeps, repeated, or omitted. One or more steps of the method 700 may be performed by the system 100.

The method 700 may include capturing one or more images of a sample, as at 702. For example, this may include capturing the image 200A that includes the sample 210A. The image 200A may be captured with the camera 110.

The method 700 may also include applying one or more filters 112, 114, 116 to the image(s) 200A, as at 704. As mentioned above, the filters 112, 114, 116 may be applied to the camera 110 and/or by the computing system 120. The filters 112, 114, 116 may be or include bandpass filters that are configured to pass the predetermined wavelength range. As mentioned above, for hemoglobin, the predetermined wavelength range may be from about 450 nm to about 690 nm, about 575 nm to about 625 nm, or about 600 nm to about 650 nm.

The filters 112, 114, 116 may each be configured to pass different wavelengths. The first filter 112 may be configured to pass a first wavelength, the second filter 114 may be configured to pass a second wavelength, and the third filter 116 may be configured to pass a third wavelength. The third wavelength may be between the first and second wavelengths. In one example, the first wavelength may be from about 639 nm to about 647 nm, the second wavelength may be from about 623 nm to about 631 nm, and the third wavelength may be from about 628 nm to about 636 nm. In another example, the first wavelength may be about 643 nm, the second wavelength may be about 627 nm, and the third wavelength may be about 632 nm.

The method 700 may also include detecting a spectral signature 510 in the image(s) 200A, as at 706. The spectral signature 510 (e.g., V-shape and/or W-shape) may be detected by the computing system 120. The spectral signature 510 may be detected after the filters 112, 114, 116 are applied to the image 200A. The spectral signature 510 may be specific to the molecule (e.g., hemoglobin) that is being detected. As mentioned, the spectral signature 510 may include one or more absorption features 520A, 520B.

In one embodiment, detecting the spectral signature 510 may include performing continuum removal on the spectral signature 510, as at 708. The continuum removal may be performed within the predetermined wavelength range. The continuum removal may be performed using linear interpolation to remove a slope from the spectral signature 510 while maintaining the absorption feature(s) (e.g., absorption feature 520A). In one example, performing the continuum removal may include:

$$w * r(\lambda 1) + (1 - w) * r(\lambda 2) \quad \text{Equation 1}$$

where w represents a weight value, $r(\lambda 1)$ represents the value of the spectrum of the absorption feature 520A at the first wavelength, and $r(\lambda 2)$ represents the value of the spectrum of the absorption feature 520A at the second wavelength. The weight value w may be specific for the particular molecule to be detected. For example, the weight value w may be 0.5156 for hemoglobin.

In other words, performing the continuum removal may include determining a first product of a weight and a value of a spectrum of the absorption feature 520A at the first wavelength, determining a second product of a complement of the weight and a value of the spectrum of the absorption feature 520A at the second wavelength, and determining a sum of the first product and the second product.

Detecting the spectral signature 510 may also or instead include determining a band ratio of an absorption feature 520A in the spectral signature 510, as at 610. The band ratio may be determined after the continuum removal is performed. In one example, the band ratio may include:

$$\text{Band ratio} = (w * r(\lambda 1) + (1 - w) * r(\lambda 2))/r(\lambda 3) \quad \text{Equation 2}$$

where $r(\lambda 3)$ represents the value of the spectrum of the absorption feature 520A at the third wavelength. In other words, the numerator of the band ratio may include the sum (from Equation 1), and the denominator of the band ratio may include the value of the spectrum of the absorption feature 520A at the third wavelength.

In one embodiment, the image 200A may include a plurality of pixels, and the spectral signature 510 may be detected (e.g., the band ratio may be determined) for one or more of the pixels. For example, the spectral signature 510 may be detected (e.g., the band ratio may be determined) for all of the pixels in the image 200A.

The method 700 may also include aggregating the band ratios for the pixels in the image 200A, as at 712. One or more techniques may be used to aggregate the band ratios. For example, one technique includes aggregating or counting the number of values above a specific threshold, and another technique includes aggregating or counting values over a specific spatial area. In one embodiment, one of the techniques may be used when the concentration of the molecule in the sample is below a predetermined concentration threshold, and the other technique may be used when the concentration of the molecule in the sample is above the predetermined concentration threshold. In another embodiment, multiple techniques may be combined to create a composite.

The method 700 may also include determining that the molecule (e.g., hemoglobin) is present in the sample 210A, as at 714. The determination that the molecule is present may be based at least partially upon the detection of the spectral signature 510, the determination of the band ratio, the aggregation of the band ratios, or a combination thereof. The method 700 may be able to detect a predetermined mass of the molecule (e.g., hemoglobin) within one gram of the sample 210A (e.g., stool+hemoglobin). The predetermined mass may be from about 5 micrograms to about 10 micrograms or about 10 micrograms to about 20 micrograms, which is less than or equal to the threshold used by conventional FIT tests in the United States (i.e., 20 micrograms hemoglobin/gram stool).

The method 700 may also include determining an amount of the molecule that is present in the sample 210A, as at 716. The determination of the amount of the molecule that is present may be based at least partially upon the detection of the spectral signature 510, the determination of the band ratio, the aggregation of the band ratios, other mathematical approaches, or a combination thereof. In another embodiment, the determination of the amount of the molecule that is present may be a function of the band ratio scores from the pixels of the sample. The use of "function" can represent any algorithm that takes as input the band ratio scores and generates a number that is assigned to the sample.

The method 700 may also include confirming that the molecule (e.g., hemoglobin) is present in the sample 210A using the testing device 130, as at 718. This may also or instead include determining an amount of the molecule that is present in the sample 210A using the testing device 130. This step may occur before, simultaneously with, or after one or more of the steps 702-716. For example, this step may occur in response to the image-based determination(s) at step 714 and/or step 716.

In another embodiment, instead of or in addition to using the testing device 130 (e.g., a FIT test), additional diagnostic information may be obtained for the patient. For example, the patient history or lab data for the patient may be used to generate a composite score that includes multiple risk variables beyond spectral and FIT alone.

The method 700 may also include performing a colonoscopy, as at 720. The colonoscopy may be performed at least partially in response to the determination that the molecule is present (at 714), the determination of the amount of the molecule that is present (at 716), the determination that the molecule is present (at 718), or a combination thereof.

Although the present disclosure has been described in connection with preferred embodiments thereof, it will be appreciated by those skilled in the art that additions, deletions, modifications, and substitutions not specifically described may be made without departing from the spirit and scope of the disclosure as defined in the appended claims.

The invention claimed is:

1. A method for detecting a molecule in a sample, the method comprising:
   applying a first filter to an image at a first wavelength;
   applying a second filter to the image at a second wavelength;
   applying a third filter to the image at a third wavelength, wherein the first, second, and third wavelengths are within a predetermined wavelength range, and wherein the first, second, and third wavelengths are different from one another;
   detecting a spectral signature for the molecule in the sample in the image after the first, second, and third filters are applied to the image, wherein detecting the spectral signature comprises:
      performing continuum removal on the spectral signature within the predetermined wavelength range; and
      determining a band ratio of an absorption feature of the spectral signature after the continuum removal is performed; and
   determining whether the molecule is present in the sample based at least partially upon the detected spectral signature, wherein the molecule is determined to be present in the sample based at least partially upon the band ratio.

2. The method of claim 1, wherein the molecule comprises hemoglobin, wherein the sample comprises a stool sample, and wherein the spectral signature comprises a V-shaped portion of a curve or a W-shaped portion of a curve on a reflectance versus wavelength graph.

3. The method of claim 2, wherein determining whether the molecule is present comprises determining that the molecule is present, and wherein the method further comprises:
   confirming that the hemoglobin is present in the stool sample using a fecal immunochemical test (FIT); and
   performing a colonoscopy on a person from whom the sample was collected after the hemoglobin is confirmed to be present.

4. The method of claim 1, wherein the predetermined wavelength range is between 450 nm and 690 nm, and wherein the third wavelength is between the first and second wavelengths.

5. The method of claim 1, wherein the continuum removal is performed using linear interpolation to remove a slope from the spectral signature while maintaining the absorption feature.

6. The method of claim 1, wherein performing the continuum removal comprises:
   determining a first product of a weight and a value of the absorption feature at the first wavelength;
   determining a second product of a complement of the weight and a value of the absorption feature at the second wavelength; and
   determining a sum of the first product and the second product.

7. The method of claim 6, wherein the band ratio comprises a ratio of the sum and the value of the absorption feature at the third wavelength.

8. The method of claim 1, wherein the band ratio is determined for each pixel in the image.

9. The method of claim 8, further comprising determining an amount of the molecule that is present in the sample based at least partially upon an aggregation of the band ratios.

10. A method for detecting hemoglobin in a stool sample, the method comprising:
    capturing an image of the stool sample with a camera;
    applying a first bandpass filter to the image at a first wavelength as the image is captured;
    applying a second bandpass filter to the image at a second wavelength as the image is captured;
    applying a third bandpass filter to the image at a third wavelength as the image is captured, wherein the first, second, and third wavelengths are between 450 nm and 690 nm, and wherein the third wavelength is between the first and second wavelengths;
    detecting a spectral signature for the hemoglobin in the stool sample in the image after the first, second, and third bandpass filters are applied to the image, wherein the spectral signature comprises an absorption feature, and wherein detecting the spectral signature comprises:
       performing continuum removal on the spectral signature between 450 nm and 690 nm using linear interpolation to remove a slope from the spectral signature while maintaining the absorption feature, wherein performing the continuum removal comprises:
          determining a first product of a weight and a value of the absorption feature at the first wavelength;
          determining a second product of a complement of the weight and a value of the absorption feature at the second wavelength; and
          determining a sum of the first product and the second product; and
       determining a band ratio of the absorption feature for each pixel in the image, wherein the band ratio comprises a ratio of the sum and the value of the absorption feature at the third wavelength;
    aggregating the band ratios for the pixels in the image; and
    determining that the hemoglobin is present in the stool sample based at least partially upon the aggregation of the band ratios.

11. The method of claim 10, wherein the first wavelength is from about 639 nm to about 647 nm, the second wavelength is from about 623 nm to about 631 nm, and the third wavelength is from about 628 nm to about 636 nm.

12. The method of claim 10, wherein the spectral signature comprises a V-shaped portion of a curve or a W-shaped portion of a curve on a reflectance versus wavelength graph.

13. The method of claim 10, further comprising determining an amount of the hemoglobin that is present in the stool sample based at least partially upon the aggregation of the band ratios.

14. The method of claim 10, further comprising confirming that the hemoglobin is present in the stool sample using fecal immunochemical test (FIT) after the hemoglobin is determined to be present in the stool sample.

* * * * *